US012629372B2

(12) United States Patent
Lee et al.

(10) Patent No.: US 12,629,372 B2
(45) Date of Patent: May 19, 2026

(54) DEVELOPMENT OF COMBINED THERAPEUTIC AGENT FOR FIBROTIC DISEASE

(71) Applicant: Korea Institute of Radiological & Medical Sciences, Seoul (KR)

(72) Inventors: Yoon Jin Lee, Seoul (KR); Hae June Lee, Seoul (KR); Kwang Seok Kim, Seoul (KR); Ji Hee Kim, Seoul (KR); Jae Kyung Nam, Seoul (KR)

(73) Assignee: Korea Institute of Radiological & Medical Sciences, Seoul (KR)

( * ) Notice: Subject to any disclaimer, the term of this patent is extended or adjusted under 35 U.S.C. 154(b) by 760 days.

(21) Appl. No.: 17/914,011

(22) PCT Filed: Mar. 17, 2021

(86) PCT No.: PCT/KR2021/003291
§ 371 (c)(1),
(2) Date: Nov. 28, 2022

(87) PCT Pub. No.: WO2021/194153
PCT Pub. Date: Sep. 30, 2021

(65) Prior Publication Data

US 2023/0133499 A1 May 4, 2023

(30) Foreign Application Priority Data

Mar. 24, 2020 (KR) ........................ 10-2020-0035320

(51) Int. Cl.

| | |
|---|---|
| ***A61K 31/506*** | (2006.01) |
| ***A23L 33/10*** | (2016.01) |
| ***A61K 31/155*** | (2006.01) |
| ***A61P 1/16*** | (2006.01) |
| ***A61P 11/00*** | (2006.01) |

(52) U.S. Cl.
CPC ............ *A61K 31/506* (2013.01); *A23L 33/10* (2016.08); *A61K 31/155* (2013.01); *A61P 1/16* (2018.01); *A61P 11/00* (2018.01)

(58) Field of Classification Search
CPC ....... A61K 31/155; A61K 31/506; A61P 1/16; A61P 11/00
See application file for complete search history.

(56) References Cited

FOREIGN PATENT DOCUMENTS

| | | | |
|---|---|---|---|
| CN | 107982247 | A | 5/2018 |
| CN | 109477072 | A | 3/2019 |
| JP | 2018-9022 | A | 1/2018 |
| JP | 2018-009022 | A | 1/2018 |
| JP | 6469643 | B2 | 2/2019 |
| KR | 10-2014-013567 | A | 11/2014 |
| KR | 10-2014-0135617 | A | 11/2014 |
| KR | 10-2019-0074480 | A | 6/2019 |
| WO | WO2016140714 | A1 | 9/2016 |
| WO | WO201799250 | A1 | 11/2017 |
| WO | WO2017199250 | A1 | 11/2017 |
| WO | WO2019052556 | A1 | 3/2019 |
| WO | WO2019125016 | A1 | 6/2019 |

OTHER PUBLICATIONS

Todd et al., "Molecular and cellular mechanisms of pulmonary fibrosis.", Fibrogenesis & Tissue Repair 2012, 5(1):11.
Gross et al., "Idiopathic Pulmonary Fibrosis", New England Journal of Medicine, Aug. 16, 2001, 345(7): 517.
Wynn, "Fibrotic Disease and the TH1/TH2 Paradigm", Nat Rev Immunol. Aug. 2004; 4(8): 583-594.
Friedman et al., "Therapy for Fibrotic Diseases: Nearing the Starting Line.", Science Translation Medicine, 5 (167):1-17, Jan. 2013.
Wang et al., Attenuation of metformin on radiation-induced lung fibrosis in rats, Chin J Radiol Med Prot, Oct. 2017, 37(10):736-741: Abstract Only.
Xiao et al., Metformin protects against bleomycin-induced pulmonary fibrosis in mice, Natl Med J China, Jun. 26, 2018, 98(24): 1951-1955: Abstract Only.
Yao et al., Research Progress on the Relationship between the Wnt/β-catenin Signaling Pathway and Pulmonary Fibrosis), PJCCPVD, Jul. 2017, 25:226-228: Abstract Only.
Deng et al., Effect of metformin adjuvant therapy on liver fibrosis and insulin resistance in patients with NAFLD, China Medicine and Pharmacy, Oct. 2018, 8(19): 92-94: Abstract Only.
Song et al., Identification of radiation-induced EndMT inhibitors through cell-based phenomic screening, FEBS Open Bio. Dec. 6, 2018;9(1): 82-91.
Yahyapour et al., Protective Effect of Metformin, Resveratrol and Alpha-lipoic Acid on Radiation-Induced Pneumonitis and Fibrosis: A Histopathological Study, Curr Drug Res Rev. 2019; 11(2): 111-117.
Mazza et al., The Role of Metformin in the Management of NAFLD, Exp Diabetes Res. 2012:2012:716404.

*Primary Examiner* — Kevin E Weddington

(74) *Attorney, Agent, or Firm* — Bret E. Field; Bozicevic, Field & Francis LLP

(57) ABSTRACT

The present disclosure relates to a composition of a complex comprising metformin and Chir99021 for treating fibrosis. The composition according to the present disclosure inhibits collagen deposition and inflammatory responses and prevents vascular fibrosis and tissue damage, thereby exhibiting excellent prevention and therapeutic effects against fibrosis.

2 Claims, 6 Drawing Sheets

【Fig. 1】
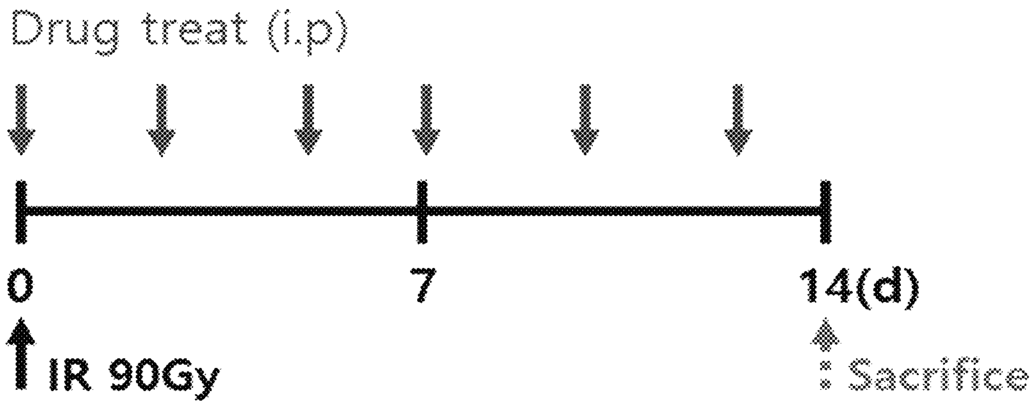
【Fig. 2】
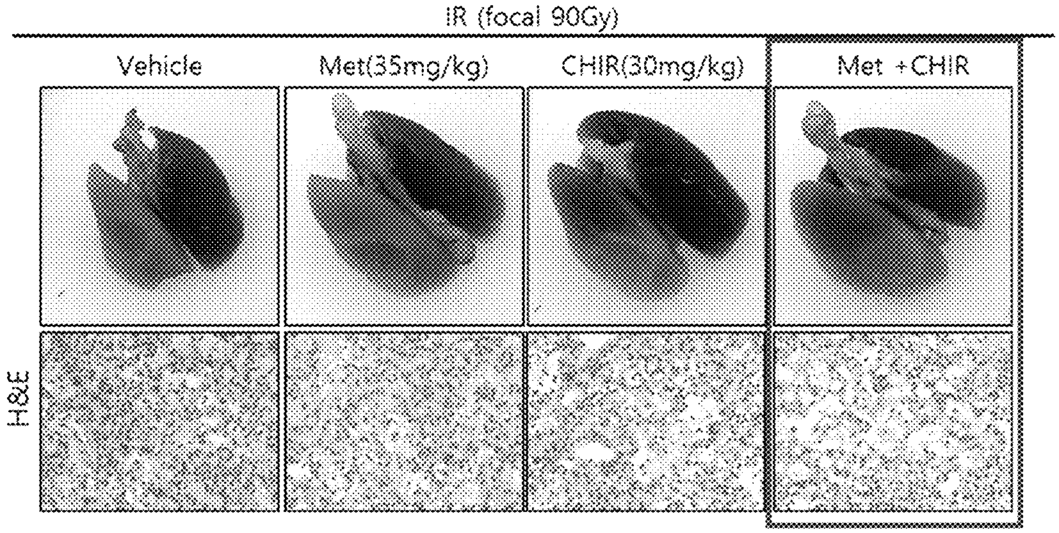

【Fig. 3】
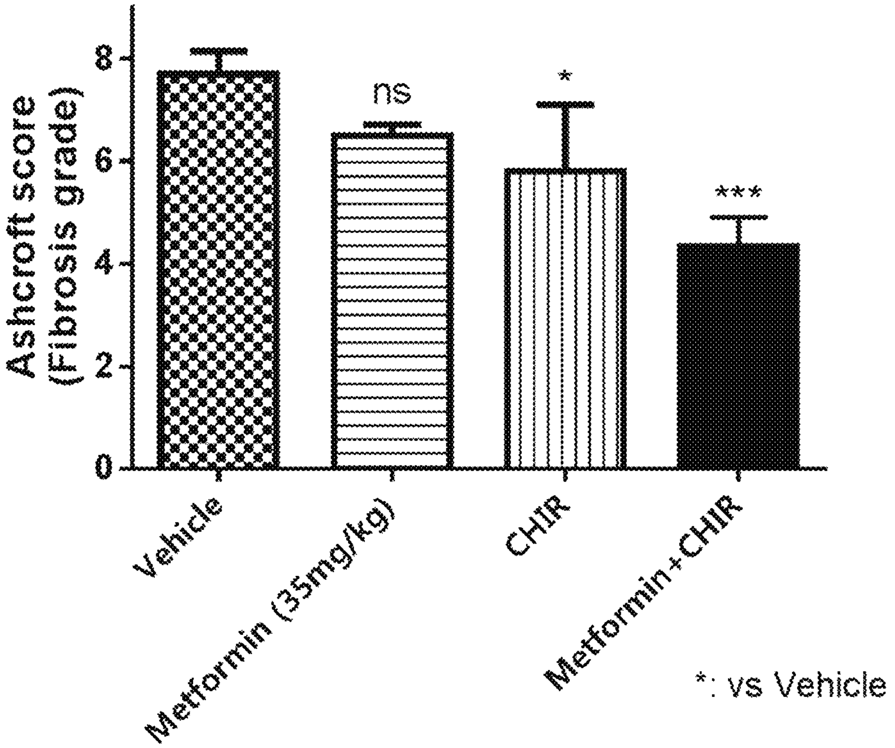
【Fig. 4】
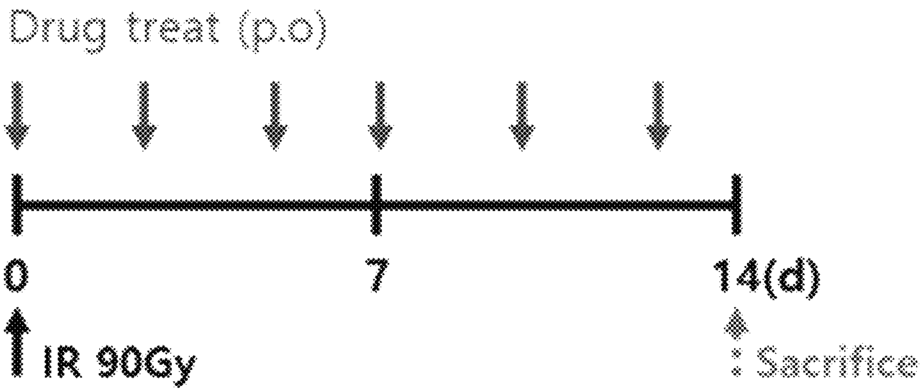

【Fig. 5】
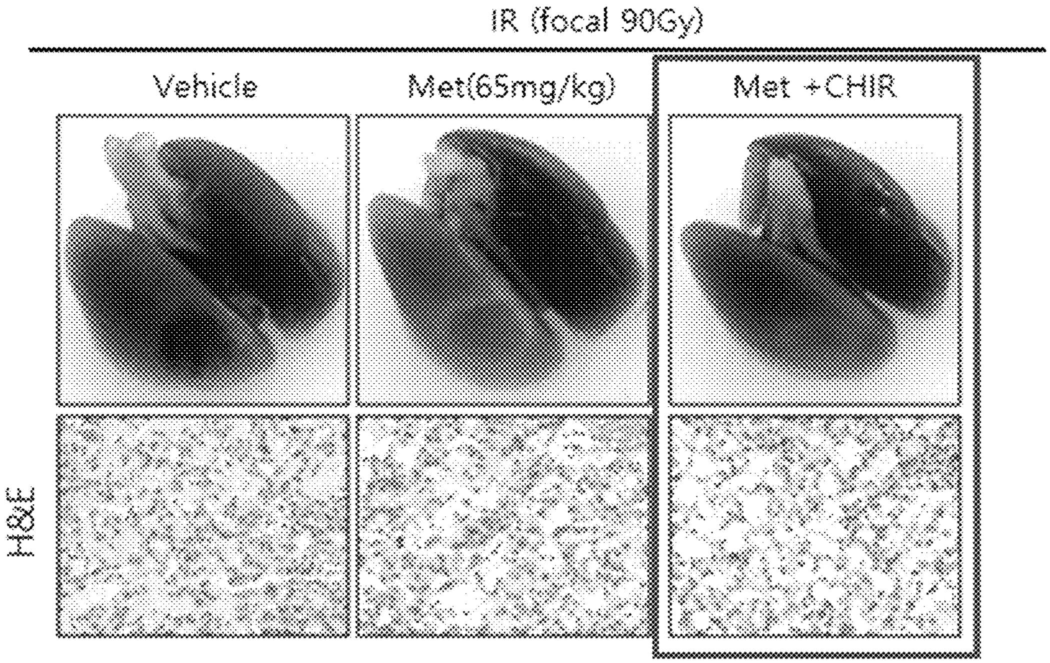

【Fig. 6】
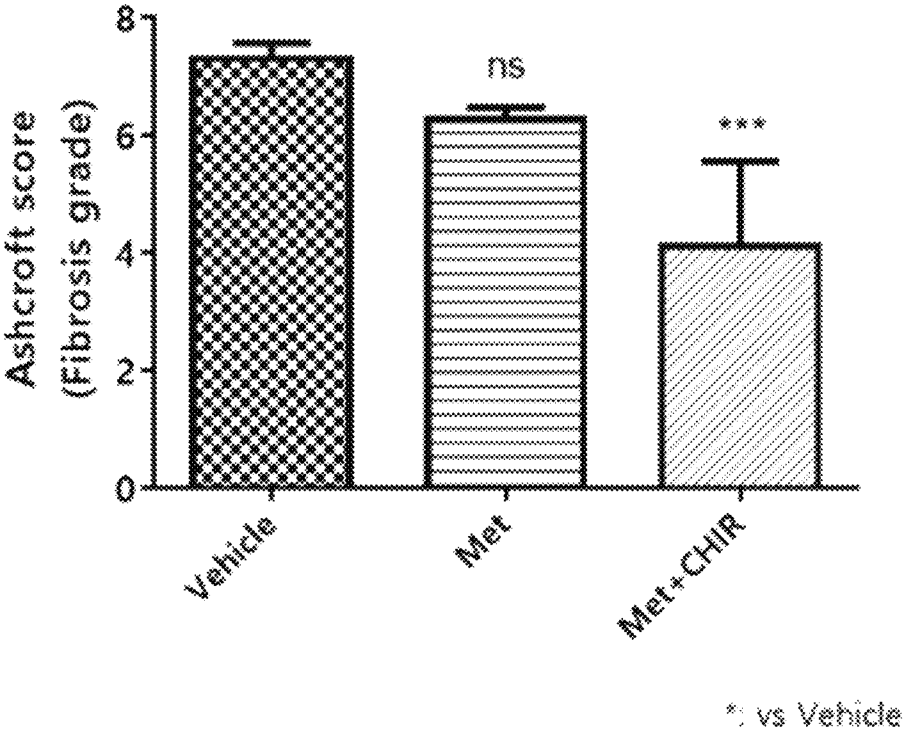
【Fig. 7】
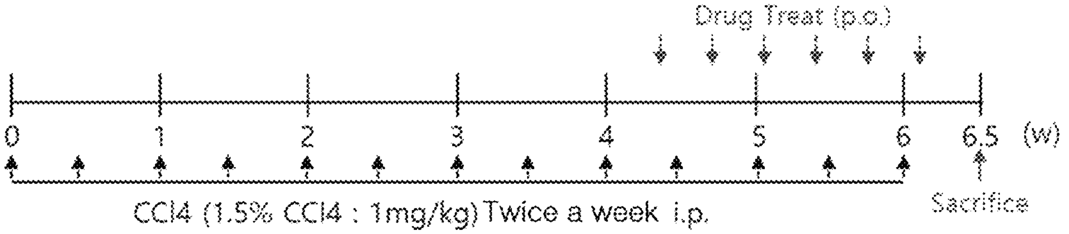

【Fig. 8】
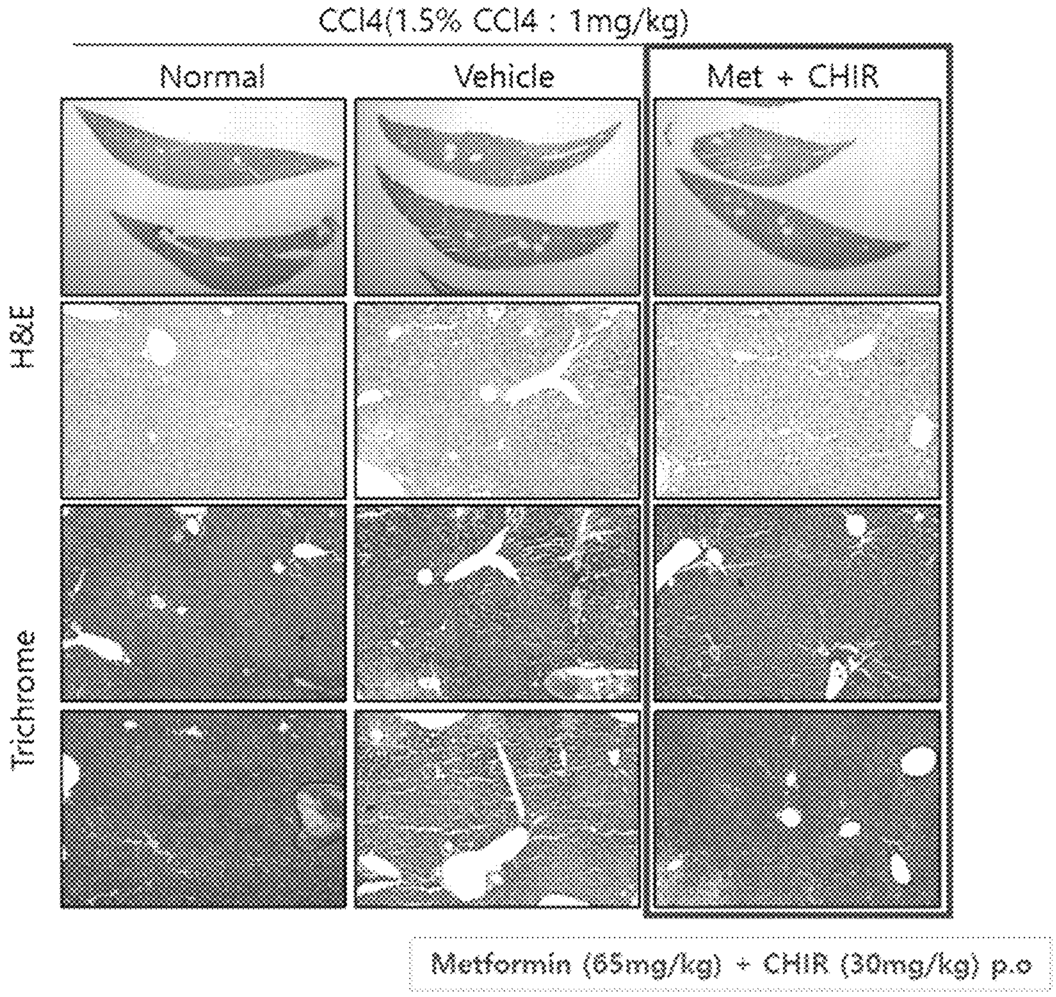

【Fig. 9】
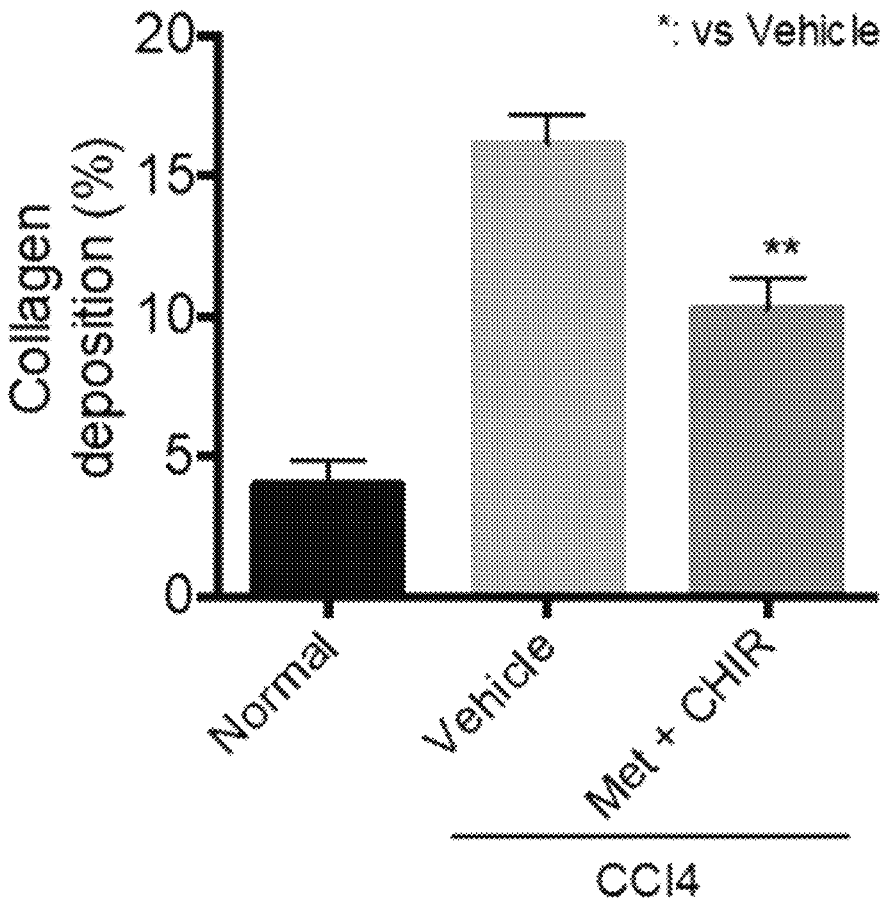

DEVELOPMENT OF COMBINED THERAPEUTIC AGENT FOR FIBROTIC DISEASE

TECHNICAL FIELD

The present disclosure relates to a combined composition for the prevention or treatment of fibrosis.

BACKGROUND ART

Fibrosis is a disease in which abnormal production, accumulation and deposition of an extracellular matrix occurs by fibroblasts, and is caused by fibrosis of an organ or tissue. The fibrosis is a very fatal disease that causes organ damage. As an example, idiopathic pulmonary fibrosis (IPF) results from recurrent alveolar epithelial cell damage associated with fibroblast accumulation and myofibroblast differentiation, and is a chronic, progressive, and lethal disease that causes excessive accumulation of extracellular matrix (ECM) with irreversible destruction of lung parenchyma tissue. However, since there is no effective treatment for fibrosis so far (Fibrogenesis Tissue Repair, 2012, 5(1): 11; N Engl J Med, 2001, 345(7): 517), there is a continuous demand for the development of therapeutic agents capable of effectively preventing or treating fibrosis.

Fibrosis occurs as a result of various underlying diseases. Chronic inflammation or tissue damage/remodeling is a typical fibrosis inducing case. Specific disease examples include idiopathic pulmonary fibrosis (IPF), liver fibrosis associated with alcoholic and nonalcoholic liver cirrhosis, renal fibrosis, cardiac fibrosis, and keloid formation resulting from abnormal wound healing [Wynn, T. A. (2004) Nature Reviews Immunology. 4: 583-594; Friedman, S. L. (2013) Science Translation Medicine. 5(167):1-17]. Additionally, the fibrosis is a key pathological feature associated with chronic autoimmune diseases including rheumatoid arthritis, Crohn's disease, systemic erythematosus lupus and scleroderma. Diseases that represent a serious unmet medical need include idiopathic pulmonary fibrosis (IPF), scleroderma and liver fibrosis associated with nonalcoholic steatohepatitis (NASH). The increased incidence of NASH-associated liver fibrosis is expected to be directly similar to that of type 2 diabetes and obesity.

In particular, radiation-induced lung fibrosis (RILF) is the most common complication after stereotactic body radiotherapy (SBRT), and a very serious complication that occurs due to the accumulation of fibroblasts, myofibroblasts and leukocytes, increases extracellular matrix proteins such as collagen, and threatens life due to respiratory disorders. Accordingly, it is recognized that side effects of RILF may be induced during radiation therapy, but studies for treating RILF are insufficient.

On the other hand, liver fibrosis (or hepatic fibrosis) or liver cirrhosis belongs to disease caused while liver tissue is repeatedly damaged and regenerated to cause hepatitis, hepatitis develops into liver fibrosis, and liver fibrosis develops into liver cirrhosis again. Liver fibrosis is liver fibrogenesis that occurs due to the continuous destruction of hepatocytes and repeated liver damage, in which the production of extracellular matrix (ECM) is increased, but its degradation is relatively decreased, and if getting worse, liver fibrosis develops into liver cirrhosis, liver failure or liver cancer. Liver fibrosis is difficult to restore to a normal liver once fibrosis progresses, and develops into liver cirrhosis or liver cancer, resulting in a continuous increase in mortality. Liver cirrhosis refers to a decrease in liver function by changing normal liver tissue to fibrosis tissue such as regenerative nodules (a phenomenon in which small lumps are formed) due to chronic inflammation. So far, there has been no specific treatment for these diseases.

The present inventors have made many efforts to develop a composition for the prevention or treatment of fibrosis, and as result, found a combined preparation exhibiting preventive and therapeutic effects against fibrosis in a radiation-induced lung fibrosis mouse model, a nonalcoholic liver fibrosis mouse model, and the like, and then completed the present disclosure.

DISCLOSURE

Technical Problem

An object of the present disclosure is to provide a pharmaceutical composition for the prevention or treatment of fibrosis, comprising metformin or a pharmaceutically acceptable salt thereof; and Chir99021 or a pharmaceutically acceptable salt thereof as an active ingredient.

Another object of the present disclosure is to provide a method for the prevention or treatment of fibrosis, comprising administering metformin or a pharmaceutically acceptable salt thereof; and Chir99021 or a pharmaceutically acceptable salt thereof to a subject.

Yet another object of the present disclosure is to provide a food composition for the prevention or improvement of fibrosis, comprising metformin or a food acceptable salt thereof; and Chir99021 or a food acceptable salt thereof.

Technical Solution

Specifically, this will be described as follows. Meanwhile, each description and embodiment disclosed in the present disclosure can also be applied to each of other descriptions and embodiments. That is, all combinations of various components disclosed in the present disclosure belong to the scope of the present disclosure. In addition, the specific description described below may not limit the scope of the present disclosure.

An aspect of the present disclosure for achieving the object provides a pharmaceutical composition for the prevention or treatment of fibrosis, comprising metformin or a pharmaceutically acceptable salt thereof; and Chir99021 or a pharmaceutically acceptable salt thereof as an active ingredient.

The metformin may be a compound represented by Chemical Formula 1 below

[Chemical Formula 1]

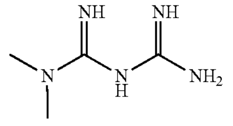

The compound represented by Chemical Formula 1 may be referred to as N,N-dimethylimidodicarbonimidic diamide.

The compound of Chemical Formula 1 may be prepared using conventional knowledge known in the field of organic chemistry, or used by purchasing a commercially available compound.

The Chir99021 may be a compound represented by Chemical Formula 2 below.

[Chemical Formula 2]

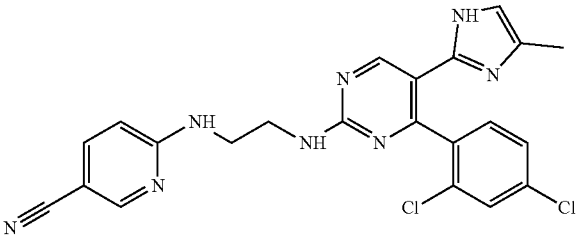

The compound represented by Chemical Formula 2 may be referred to as 6-((2-((4-(2,4-Dichlorophenyl)-5-(4-methyl-1H-imidazol-2-yl)pyrimidin yl)amino)ethyl)amino) nicotinonitrile.

The compound of Chemical Formula 2 may be prepared using conventional knowledge known in the field of organic chemistry, or used by purchasing a commercially available compound.

In the present disclosure, the "pharmaceutically acceptable salt" refers to salts commonly used in the pharmaceutical industry. For example, the pharmaceutically acceptable salt includes inorganic ion salts prepared from calcium, potassium, sodium, magnesium, etc.; inorganic acid salts prepared from hydrochloric acid, nitric acid, phosphoric acid, hydrobromic acid, iodic acid, perchloric acid, sulfuric acid, etc.; organic acid salts prepared from acetic acid, trifluoroacetic acid, citric acid, maleic acid, succinic acid, oxalic acid, benzoic acid, tartaric acid, fumaric acid, manderic acid, propionic acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, etc.; sulfonic acid salts prepared from methanesulfonic acid, ethanesulfonic acid, benzenesulfonic acid, p-toluenesulfonic acid, naphthalenesulfonic acid, etc.; amino acid salts prepared from glycine, arginine, lysine, etc.; and amine salts prepared from trimethylamine, triethylamine, ammonia, pyridine, picoline, etc. However, the types of salts in the present disclosure are not limited to these listed salts.

As used herein, the term "fibrosis" refers to the formation of an excess of fibrous connective tissue in an organ or tissue. The fibrous connective tissue may be distinguished from fibrous tissue as a normal component in an organ or tissue. Due to the excessive accumulation of an extracellular matrix such as fibronectin and collagen by fibroblasts, fibrosis may be understood as a fatal disease that ultimately causes organ damage.

In the present disclosure, the fibrosis may include fibrosis-related diseases occurring in all tissues, such as lung, kidney, liver, heart, brain, blood vessels, joint, intestine, skin, soft tissue, bone marrow, penis, peritoneum, muscle, spine, testis, ovary, breast, thyroid gland, tympanic membrane, pancreas, gallbladder, bladder or prostate.

Specifically, in the present disclosure, the fibrosis is a disease caused by fibrosis occurring in each tissue of the body, and for example, may include abnormal wound healing, lung fibrosis (radiation-induced lung fibrosis, idiopathic pulmonary fibrosis, etc.), liver fibrosis (e.g., alcoholic liver damage induced liver fibrosis, nonalcoholic liver fibrosis, etc.), connective fibrosis, Crohn's disease (fibrosis of the intestine), cystic fibrosis of the pancreas and lung, injectable fibrosis, which especially may occur as a complication of intramuscular injection in children, endomyocardial fibrosis or cardiac fibrosis, fibrosis by Graft-Versus-Host Disease (GVHD), fibrosis of the spleen, fibrosis of the eye including retinal fibrosis, fibrosis complications of surgery or injection fibrosis, glomerulonephritis, interstitial fibrosis, Keloids and hypertrophic scars (fibrosis of the skin), macular degeneration, mediastinal fibrosis (soft tissue fibrosis of the mediastinum), morphea, multifocal fibrosis, myelofibrosis, renal systemic fibrosis (fibrosis of the skin), nodular epidermal fibrosis (e.g., benign fibrous histiocytoma), pleural fibrosis, fibrosis as a result of surgery (e.g., surgical transplant), proliferative fibrosis, pipestem fibrosis, postfibrinous fibrosis, progressive multiple fibrosis (a type of fibrosis of the lungs, a complication of coal workers' pneumoconiosis), long-lasting myocardial infarction (fibrosis of the heart), pancreatic fibrosis, progressive multiple fibrosis, radiation fibrosis, renal fibrosis, renal fibrosis associated with or causing chronic kidney disease, retroperitoneal fibrosis (fibrosis of the soft tissue of the retroperitoneum), post-surgical scarring, scleroderma/systemic sclerosis (fibrosis of the skin), epitheliosis, uterine fibrosis, or viral hepatitis induction fibrosis, but is not limited thereto.

The fibrosis may be specifically lung fibrosis or liver fibrosis.

In the present disclosure, the lung fibrosis may include idiopathic pulmonary fibrosis, nonspecific interstitial pneumonia, acute interstitial pneumonia, cryptogenic organizing pneumonia, respiratory bronchiolitis associated interstitial lung, desquamative interstitial pneumonia, lymphoid interstitial pneumonia, interstitial lung disease, diffuse lung fibrosis, radiation-induced lung fibrosis, and the like, but is not limited thereto.

Specifically, the lung fibrosis may be idiopathic pulmonary fibrosis or radiation-induced lung fibrosis.

In the present disclosure, "radiation-induced lung fibrosis (RILF)" refers to a disease in which interstitial tissues of the lung become hardened like fibers due to causes such as radiation therapy, and causes severe breathing difficulties. The radiation-induced lung fibrosis is a disease that occurs as side effects of therapy through 3D radiation therapy (3DRT), which is one of the main therapies for lung cancer patients. This disease is broadly included in the subconcept of idiopathic pulmonary fibrosis, but exhibits distinct features in its cause of disease.

The idiopathic pulmonary fibrosis is presumed to occur by various causes such as environment and viruses, but the cause is not clear, and has a difference that the radiation-induced lung fibrosis is caused by irradiation.

In the present disclosure, the "liver fibrosis" refers to a process of wound healing that occurs by conjugating collagen and extracellular matrix (ECM) secreted in large amounts from active hepatic stellate cells as inflammatory responses continues due to tissue damage. If the liver fibrosis continues to progress, a large amount of collagen is deposited in liver tissue, and the regenerative nodules are surrounded by the collagen and may develop into liver cirrhosis, which has an abnormal structure.

The liver fibrosis may be preferably nonalcoholic liver fibrosis.

The nonalcoholic liver fibrosis may be caused from nonalcoholic steatohepatitis (NASH) or non-alcoholic fatty liver disease (NAFLD), and liver cirrhosis.

As used herein, the term "treatment" refers to any action that improves or beneficially changes the symptoms of fibrosis by administration of the pharmaceutical composition, and "prevention" means any action that inhibits or delays the onset of fibrosis by administration of the pharmaceutical composition.

In the present disclosure, it was found that metformin or the pharmaceutically acceptable salt thereof; and Chir99021 or the pharmaceutically acceptable salt thereof have effects of inhibiting and treating fibrosis in radiation-induced lung fibrosis and nonalcoholic liver fibrosis. In particular, it is first confirmed that a combination thereof has a remarkable synergistic effect, and thus, it was found that metformin or the pharmaceutically acceptable salt thereof; and Chir99021 or the pharmaceutically acceptable salt thereof can be used for preventing and treating fibrosis.

Particularly, in the embodiments of the present disclosure, as a result of performing an animal experiment using radiation-induced lung fibrosis mice, in the case of administering metformin or the pharmaceutically acceptable salt thereof; and Chir99021 or the pharmaceutically acceptable salt thereof, it was confirmed that tissue damage and collagen deposition were significantly reduced in vivo, which exhibited an excellent therapeutic effect while exhibiting the same synergistic effect regardless of a route of administration.

In addition, as a result of performing an animal experiment using nonalcoholic liver fibrosis-induced mice, in the case of administering metformin or the pharmaceutically acceptable salt thereof; and Chir99021 or the pharmaceutically acceptable salt thereof, it was confirmed that tissue damage and collagen deposition were significantly reduced in vivo.

Therefore, the composition of the present disclosure has excellent preventive and therapeutic effects against fibrosis, and thus can be very usefully used for the prevention and treatment of fibrosis.

In addition, the pharmaceutical composition of the present disclosure may further include suitable carriers, excipients, or diluents, which are commonly used in the preparation of the pharmaceutical composition. The composition including the pharmaceutically acceptable carrier may have various oral or parenteral formulations. When the composition is formulated, the formulations may be prepared by using diluents or excipients, such as a filler, an extender, a binder, a wetting agent, a disintegrating agent, a surfactant, etc., which are generally used. Solid formulations for oral administration may include tablets, pills, powders, granules, capsules, and the like, and the solid formulations may be prepared by mixing at least one excipient, for example, starch, calcium carbonate, sucrose or lactose, gelatin, and the like with at least one compound. Further, lubricants such as magnesium stearate and talc and the like, may also be used in addition to general excipients. Liquid formulations for oral administration may correspond to suspensions, oral liquids, emulsions, syrups, and the like, and may include various excipients, for example, a wetting agent, a sweetener, an aromatic agent, a preserving agent, and the like, in addition to water and liquid paraffin which are commonly used as simple diluents. Formulations for parenteral administration may include a sterile aqueous solution, a non-aqueous solution, a suspension, an emulsion, a lyophilizing agent, and a suppository. As the non-aqueous solution and the suspension, propylene glycol, polyethylene glycol, vegetable oil such as olive oil, injectable ester such as ethyl oleate, and the like may be used. As a base of the suppository, witepsol, macrogol, tween 61, cacao butter, laurinum, glycerogelatin, and the like may be used.

Further, the pharmaceutical composition of the present disclosure is not limited thereto, but may be any one formulation selected from the group consisting of tablets, pills, powders, granules, capsules, suspensions, oral liquids, emulsions, syrups, sterilized aqueous solutions, non-aqueous solvents, emulsions, lyophilized agents, and suppositories.

The composition may be administered by including the compound of Chemical Formula 1 in a dose of 10 μg/kg to 100 mg/kg and the compound of Chemical Formula 2 in a dose of 10 μg/kg to 100 mg/kg, but is not limited thereto. The composition of the present disclosure may be administered in combination with a known fibrosis therapeutic agent at a different time or at the same time, or may be applied together with a known method for treating fibrosis. In addition, the composition may be administered singly or multiply. It is important to administer an amount capable of obtaining a maximum effect with a minimal amount without side-effects by considering all the elements, which may be easily determined by those skilled in the art.

A therapeutically effective dose of each active ingredient used in complex therapy may vary according to a particular compound or pharmaceutical composition to be used, a mode of administration, a symptom to be treated, the severity of symptoms to be treated, and the species, body weight, sex, dietary status, and age of a warm-blooded animal. Accordingly, the dosage regimen using the compounds of the present disclosure is selected according to various factors including a route of administration and renal and hepatic functions of a patient. A surgeon, a clinician or a veterinarian in the art may easily determine and prescribe an effective amount of a drug required to prevent, react, or block the progression of symptoms. Optimal accuracy in achieving drug concentrations within the range that obtains efficacy without toxicity requires a regimen based on the kinetics of the availability of site-targeted drugs. This includes considering the distribution, equilibrium and clearance of the drug. Accordingly, the dosage regimen, that is, the administration level and the frequency of administration of any individual ingredient of the combination of the present disclosure to be described below, may be adjusted to provide an optimal therapeutic response.

"Co-administration" means administering the ingredients of the composition of the present disclosure together or substantially simultaneously, for example, in the same vehicle or in separate vehicles in less than 15 minutes, and according to administration, for example, both compounds may exist in the gastrointestinal tract at the same time. The compounds may be administered as a fixed combination, or may be administered in separate dosage forms. It will be appreciated that the active ingredient or the unit content of ingredients contained in an individual dose in each dosage form is not required for satisfying an effective amount in itself, and that the required effective dose may be achieved by administration of a plurality of dosage units.

In addition, the compounds of the present disclosure may be administered sequentially.

In the present disclosure, the term "administration" means introducing the pharmaceutical composition of the present disclosure to a subject by any suitable method, and the route of administration may be selected from various oral or parenteral routes as long as the composition may reach a target tissue.

The pharmaceutical composition may be administered to the subject appropriately in accordance with a conventional method, a route of administration, and a dose, which are used in the art as intended or needed. Examples of the route of administration may include oral, parenteral, subcutaneous, intraperitoneal, intrapulmonary, and intravenous routes, and the parenteral injection includes intramuscular, intravenous, intraarterial, intraperitoneal or subcutaneous route. In addition, according to a method known in the art, a dose and the number of dosage times may be appropriately selected, and the dose and the number of dosage times of the pharmaceutical composition of the present disclosure to be actually administered may be appropriately determined by various factors, such as a type of symptoms, a route of administration, sex, health condition, dietary, age and weight of a subject, and the severity of disease.

In order to prevent or treat fibrosis, the pharmaceutical composition of the present disclosure may be additionally used in combination with various methods such as hormone therapy and drug therapy.

The present disclosure provides a composition used for treating fibrosis comprising metformin or a pharmaceutically acceptable salt thereof; and Chir99021 or a pharmaceutically acceptable salt thereof.

In addition, the present disclosure provides the use of metformin or a pharmaceutically acceptable salt thereof; and Chir99021 or a pharmaceutically acceptable salt thereof in preparation of a drug for the treatment of fibrosis.

In the present disclosure, the term "pharmaceutically effective dose" refers to an amount enough to inhibit or alleviate an increase in penetrability of blood vessels at a reasonable ratio applicable to the medical use. An effective dose level may be determined according to factors including a kind of subject, the severity, age, sex, the activity of a drug, sensitivity to a drug, a time of administration, a route of administration, an excretion rate, duration of treatment, and drugs to be simultaneously used, and other factors well-known in the medical field.

As used herein, the term "subject" refers to all animals, including humans, that have or have developed fibrosis diseases of the present disclosure. It is possible to prevent or treat fibrosis by administering the pharmaceutical composition of the present disclosure to the subject.

Another aspect of the present disclosure provides a method for the prevention or treatment of fibrosis comprising administering metformin or a pharmaceutically acceptable salt thereof; and Chir99021 or a pharmaceutically acceptable salt thereof to a subject.

The use of metformin or the pharmaceutically acceptable salt thereof; and Chir99021 or the pharmaceutically acceptable salt thereof for preventing or treating fibrosis is as described above.

The present disclosure provides a food composition for the prevention or improvement of fibrosis comprising metformin or a food acceptable salt thereof; and Chir99021 or a food acceptable salt thereof as an active ingredient.

As used herein, the term "food acceptable salt" refers to a salt form that may be used in food among salts, which are substances in which cations and anions are bound by electrostatic attraction, and specific examples of the type thereof include the examples of "pharmaceutically acceptable salt" described above.

The food composition of the present disclosure may be used as a health functional food. The "health functional food" refers to food produced and processed using raw materials or ingredients with functionality, which are useful for the human body according to the Art on Health Functional Foods No. 6727, and the "functionality" means intake for adjusting nutrients for the structures and functions of the human body or obtaining a useful effect on health applications such as physiological actions.

The food composition of the present disclosure may comprise an additional ingredient to be commonly used capable of enhancing odor, taste, vision, and the like. For example, the food composition may include vitamins A, C, D, E, B1, B2, B6, and B12, niacin, biotin, folate, panthotenic acid, and the like. In addition, the food composition may include minerals such as zinc (Zn), iron (Fe), calcium (Ca), chromium (Cr), magnesium (Mg), manganese (Mn), and copper (Cu). In addition, the food composition may include amino acids such as lysine, tryptophan, cysteine, and valine. In addition, the food composition may add food additives, such as preservatives (potassium sorbate, sodium benzoate, salicylic acid, sodium dehydroacetate, etc.), disinfectants (bleaching powder and highly bleaching powder, sodium hypochlorite, etc.), antioxidants (butylhydroxyanisole (BHA), butylhydroxytoleuene (BHT), etc.), colorants (tar colorant, etc.), coloring agents (sodium nitrite, sodium nitrite, etc.), bleach (sodium sulfite), seasoning (MSG sodium glutamate, etc.), sweeteners (dulcin, cyclamate, saccharin, sodium, etc.), flavorings (vanillin, lactones, etc.), swelling agents (alum, potassium D-bitartrate, etc.), reinforcing agents, emulsifying agents, thickening agents (paste), coating agents, gum base agents, foam inhibitors, solvents, improving agents, etc. The additives may be selected according to a type of food and used in an appropriate amount.

When the food composition of the present disclosure is used as the food additive, the food composition may be added as it is or used with other foods or food ingredients, and may be appropriately used according to a general method.

For the purpose of preventing and/or improving fibrosis, the food composition of the present disclosure may comprise each of the metformin or the food acceptable salt thereof; and the Chir99021 or the food acceptable salt thereof in an amount of 0.01 to 95% by weight, preferably 1 to 80% by weight with respect to the total weight of the composition. In addition, for the purpose of preventing and/or improving fibrosis, the food composition may be produced and processed in the form of tablets, capsules, powders, granules, liquids, pills, drinks, and the like.

In addition, the present disclosure provides the use of metformin or a pharmaceutically acceptable salt thereof; and Chir99021 or a pharmaceutically acceptable salt thereof in preparation of a drug for the treatment of fibrosis. Here, the definitions of "fibrosis" and "pharmaceutically acceptable salt" are as presented above.

In addition, the present disclosure provides a method for the prevention or treatment of fibrosis comprising administering a pharmaceutically effective dose of metformin or a pharmaceutically acceptable salt thereof; and Chir99021 or a pharmaceutically acceptable salt thereof to a subject in need thereof. Here, the definitions of "fibrosis", "pharmaceutically acceptable salt", and "subject" are as presented above.

In addition, the present disclosure provides a composition comprising metformin or a pharmaceutically acceptable salt thereof; and Chir99021 or a pharmaceutically acceptable salt thereof as an active ingredient to be used for the treatment of fibrosis. Here, the definitions of "fibrosis" and "pharmaceutically acceptable salt" are as presented above.

Advantageous Effects

According to the present disclosure, metformin or the pharmaceutically acceptable salt thereof; and Chir99021 or the pharmaceutically acceptable salt thereof restore tissue damage and inhibit collagen deposition in fibrosis, prevent vascular fibrosis, and inhibit inflammation, thereby exhibiting very excellent preventive and therapeutic effects against fibrosis.

DESCRIPTION OF DRAWINGS

FIG. 1 is a schematic diagram of the preparation of a radiation-induced lung fibrosis mouse model prepared by irradiating the chest of a mouse with radiation at an intensity of 4 mm and 90 Gy, and drug administration (intraperitoneal administration) timing and dose.

FIG. 2 is a diagram showing results of confirming inflammatory responses and a degree of fibrosis at a tissue damage site according to drug administration (intraperitoneal administration) in a radiation-induced lung fibrosis mouse model through hematoxylin and eosin staining.

FIG. 3 is a diagram statistically illustrating the degree of fibrosis according to drug administration (intraperitoneal administration) in a radiation-induced lung fibrosis mouse model.

FIG. 4 is a schematic diagram of the preparation of a radiation-induced lung fibrosis mouse model prepared by irradiating the chest of a mouse with radiation at an intensity of 4 mm and 90 Gy, and drug administration (oral administration) timing and dose.

FIG. 5 is a diagram showing results of confirming inflammatory responses and a degree of fibrosis at a tissue damage site according to drug administration (oral administration) in a radiation-induced lung fibrosis mouse model through hematoxylin and eosin staining.

FIG. 6 is a diagram statistically illustrating the degree of fibrosis according to drug administration (oral administration) in a radiation-induced lung fibrosis mouse model.

FIG. 7 is a schematic diagram of the preparation of a nonalcoholic liver fibrosis mouse model induced by intraperitoneal injection of $CCl_4$ (1.5% $CCl_4$:1 mg/kg) twice a week into the liver of a mouse, and drug administration timing and dose.

FIG. 8 is a diagram illustrating results of confirming changes in inflammatory responses and a degree of fibrosis at a tissue damage site according to drug administration in a nonalcoholic liver fibrosis mouse model through hematoxylin and eosin staining and trichrome staining.

FIG. 9 is a diagram statistically illustrating the degree of collagen deposition according to drug administration in a nonalcoholic liver fibrosis mouse model.

BEST MODES OF THE INVENTION

Hereinafter, the present disclosure will be described in more detail with reference to Examples. However, these Examples are only illustrative of the present disclosure, and the scope of the present disclosure is not limited to these Examples.

Example 1: Radiation-Induced Lung Fibrosis Inhibition Test According to Combined Intraperitoneal Administration of Metformin and Chir99021

Radiation was irradiated to the chest of a mouse at an intensity of 4 mm and 90 Gy to induce radiation-induced lung fibrosis. A drug was intraperitoneally or not administered once over a total of 6 times from the day of irradiation. For drug administration, metformin (Met) (35 mg/kg), Chir99021 (CHIR) (30 mg/kg), Met+CHIR (35 mg/kg+30 mg/kg) or Vehicle (non-administered) was administered to the experimental animals A solvent composition for drug administration was used under a PBS condition for metformin, and used with a composition of 5% DMSO and 30% PEG for Chir99021.

On day 14 after irradiation, the experimental animals were sacrificed and autopsied to confirm specifically whether lung fibrosis was alleviated. A schematic diagram of the experimental process was shown in FIG. 1.

H&E staining was used to confirm inflammatory responses and fibrosis of a tissue damage site in a radiation-induced lung fibrosis mouse model. After fixing lung tissue with 10% formalin, paraffin sections were made and stained with hematoxylin and eosin. Specifically, the slid mouse tissue first reacted with xylene 3 times for 5 minutes each as a process of removing paraffin penetrated into the tissue, reacted with 100% ethanol twice, reacted with 95%, 70%, and 50% ethanol solutions for 3 minutes, respectively, and was washed with running water for 10 minutes after the 50% ethanol process was completed. The mouse tissue reacted with a hematoxylin solution for 2 minutes to stain a nucleus and was washed with running water for 10 minutes. Then, the mouse tissue reacted with an eosin solution for 30 seconds to stain a cytoplasm, reacted with 50%, 70%, 95%, and 100% ethanol processes for 1 minute, respectively, and finally reacted with a xylene solution, and then was added with a drop of mounting solution, and then covered with a cover slide and observed under a microscope.

In addition, using a trichrome staining method, fibrosis grades for living tissue were measured based on the following conditions.

| Score | Histological features |
|---|---|
| 0 | Normal lung |
| 1 | Minimal fibrous thickening of alveolar or bronchiolar walls |
| 2 | Moderate thickening of walls without obvious damage to lung |
| 3 | architecture |
| 4 | Increased fibrosis with definite damage to lung structure and |
| 5 | formation of fibrous bands or smallfibrous masses |
| 6 | Severe distortion of structure and large fibrous areas |
| 7 | |
| 8 | Total fibrous obliteration of the field |

Through hematoxylin and eosin staining, the cell nucleus may be observed in blue and the cytoplasm may be observed in pink.

The analyzed results were illustrated in FIGS. 2 and 3, respectively.

As can be seen in FIG. 2, it was found that tissue damage appeared in a non-administered group (Vehicle) after irradiation through hematoxylin and eosin staining. On the other hand, the treatment of Met+CHIR significantly improved the degree of tissue damage, which exhibited a more excellent effect than treatment of metformin alone and Chir99021 alone, respectively.

In addition, as shown in FIG. 3, as a result of statistically confirming the degree of fibrosis and the degree of collagen deposition, considering the grade of fibrosis and the degree of collagen deposition, the treatment of Met+CHIR greatly improved the lung fibrosis through a synergistic effect according to a combination thereof.

Example 2: Radiation-Induced Lung Fibrosis Inhibition Test According to Combined Oral Administration of Metformin and Chir99021

Radiation was irradiated to the chest of a mouse at an intensity of 4 mm and 90 Gy to induce radiation-induced lung fibrosis. A drug was orally or not administered once over a total of 6 times from the day of irradiation. For drug administration, metformin (Met) (65 mg/kg), Chir99021 (CHIR) (30 mg/kg), Met+CHIR (65 mg/kg+30 mg/kg) or Vehicle (non-administered) was administered to the experimental animals. A solvent composition for drug administration was used under a PBS condition for metformin, and used with a composition of 5% DMSO and 30% PEG for Chir99021.

On day 14 after irradiation, the experimental animals were sacrificed and autopsied to confirm specifically whether lung fibrosis was alleviated. A schematic diagram of the experimental process was shown in FIG. 4.

H&E staining was used to confirm inflammatory responses and fibrosis of a tissue damage site in a radiation-induced lung fibrosis mouse model. After fixing lung tissue with 10% formalin, paraffin sections were made and stained with hematoxylin and eosin. Specifically, the slid mouse tissue first reacted with xylene 3 times for 5 minutes each as a process of removing paraffin penetrated into the tissue, reacted with 100% ethanol twice, reacted with 95%, 70%, and 50% ethanol solutions for 3 minutes, respectively, and was washed with running water for 10 minutes after the 50% ethanol process was completed. The mouse tissue reacted with a hematoxylin solution for 2 minutes to stain a nucleus and was washed with running water for 10 minutes. Then, the mouse tissue reacted with an eosin solution for 30 seconds to stain a cytoplasm, reacted with 50%, 70%, 95%, and 100% ethanol processes for 1 minute, respectively, and finally reacted with a xylene solution, and then was added with a drop of mounting solution, and then covered with a cover slide and observed under a microscope.

In addition, using a trichrome staining method, fibrosis grades for living tissue were measured.

Through hematoxylin and eosin staining, the cell nucleus may be observed in blue and the cytoplasm may be observed in pink.

The analyzed results were illustrated in FIGS. 5 and 6, respectively.

As can be seen in FIG. 5, it was found that tissue damage appeared in a non-administered group (Vehicle) after irradiation through hematoxylin and eosin staining. On the other hand, the treatment of Met+CHIR significantly improved the degree of tissue damage, which exhibited a more excellent effect than treatment of metformin alone and Chir99021 alone, respectively.

In addition, as shown in FIG. 6, as a result of statistically confirming the degree of fibrosis and the degree of collagen deposition, considering the grade of fibrosis and the degree of collagen deposition, the treatment of Met+CHIR greatly improved the lung fibrosis through a synergistic effect according to a combination thereof.

Example 3. Nonalcoholic Liver Fibrosis Inhibition Test According to Combined Administration of Metformin and Chir99021

Nonalcoholic liver fibrosis was induced by intraperitoneal injection of $CCl_4$ (1.5% $CCl_4$:1 mg/kg) twice a week into the liver of a mouse. After 4.5 weeks of $CCl_4$ administration, metformin (Met) and Chir99021 (CHIR) (65 mg/kg+30 mg/kg), or vehicle (non-administered) was administered, and liver tissue damage and fibrosis were observed after 6.5 weeks. The schematic diagram thereof was illustrated in FIG. 7.

In order to confirm the inflammatory responses and fibrosis of a tissue damage site in a nonalcoholic liver fibrosis mouse model, hematoxylin and Eosin staining and trichrome staining were used similarly to Example 1. After fixing liver tissue with 10% formalin, paraffin sections were made and stained with hematoxylin and eosin and trichrome. Through hematoxylin and eosin staining, the cell nucleus may be observed in blue and the cytoplasm may be observed in pink, and through trichrome staining, the collagen deposition may be observed in blue.

In the case of trichrome staining, the mouse tissue was fixed with 10% formalin for 5 days and a paraffin block was made. In order to remove paraffin in the tissue, the mouse tissue reacted with xylene 3 times for 5 minutes each, and reacted with 100%, 95%, 75%, and 50% ethanol solutions for 3 minutes, respectively, and was washed with running water for 10 minutes after the last reaction was completed. First, the mouse tissue reacted with a Bouin's solution in a water bath at 60° C. for 1 hour. After the reaction, the mouse tissue was washed in running water for 10 minutes, mixed with Weigert's hematoxylins A and B at a 1:1 ratio, reacted for 10 minutes, and then was washed in running water for 10 minutes. Then, the mouse tissue reacted with red staining for 3 minutes and was rinsed once with tertiary distilled water, and then reacted with phosphhotunstic/phosphomolydic acid for 20 minutes and aniline blue for 30 minutes, rinsed 3 times with tertiary distilled water, and then sequentially reacted with 1% acetic acid for 1 minute. Finally, after the dehydration process and the xylene solution were finished, a drop of mounting solution was dropped, and then covered with a cover glass, and observed under a microscope.

The results thereof were illustrated in FIGS. 8 and 9.

As can be seen in FIG. 8, it could be seen that tissue damage and collagen deposition were shown in a non-administered group (Vehicle) after irradiation through hematoxylin and eosin staining and trichrome staining.

On the other hand, the administration of metformin (Met) and Chir99021 (CHIR) significantly improved the tissue damage and collagen deposition.

In particular, as can be seen in FIG. 9, administration of metformin (Met) and Chir99021 (CHIR) significantly improved collagen deposition. Furthermore, the combined administration of metformin (Met) and Chir99021 (CHIR) greatly inhibited the tissue damage and the collagen deposition through a synergistic effect to greatly improve fibrosis of liver tissue.

When combining the results, the combined administration of metformin and Chir99021 inhibits the collagen deposition in fibrosis, inhibits the inflammatory responses, prevents the vascular fibrosis and prevents the tissue damage, thereby exhibiting an excellent effect on fibrosis. In particular, the combination of these two compounds greatly improved the symptoms of fibrosis through a synergistic effect, and both showed excellent synergistic effects regardless of a route of administration.

In addition, through the animal experiments, the administration of metformin and Chir99021 showed excellent preventive and therapeutic effects against fibrosis, such as inhibiting radiation-induced lung fibrosis and nonalcoholic liver fibrosis in vivo.

Accordingly, the metformin or the pharmaceutically acceptable salt thereof; and the Chir99021 or the pharmaceutically acceptable salt thereof may be very usefully used for preventing or treating fibrosis.

It will be appreciated by those skilled in the art that the present disclosure as described above may be implemented into other specific forms without departing from the technical spirit thereof or essential characteristics. Thus, it is to be appreciated that embodiments described above are intended to be illustrative in every sense, and not restrictive. The scope of the present disclosure is represented by claims to be described below rather than the detailed description, and it is to be interpreted that the meaning and scope of the claims and all the changes or modified forms derived from the equivalents thereof come within the scope of the present disclosure.

The invention claimed is:

1. A pharmaceutical composition for inhibition radiation-induced lung fibrosis or non-alcoholic liver fibrosis, the pharmaceutical composition comprising:

metformin represented by Chemical Formula 1, or a pharmaceutically acceptable salt thereof; and Chir99021 represented by Chemical Formula 2, or a pharmaceutically acceptable salt thereof;

wherein:

Chemical Formula 1 is:

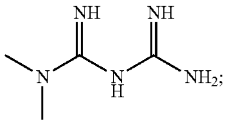

and

Chemical Formula 2 is:

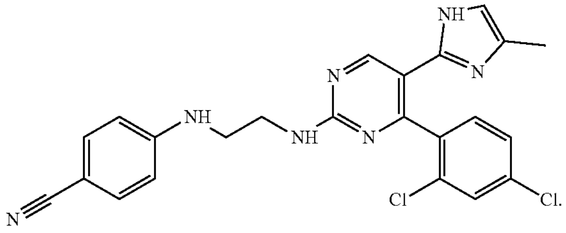 [SMILES: Cc1c[nH]c(-c2cnc(NCCNc3ccc(C#N)cc3)nc2-c2ccc(Cl)cc2Cl)n1]

2. The pharmaceutical composition of claim 1, wherein the composition is formulated for oral administration agents or injections.

* * * * *